United States Patent
Rathjen

(10) Patent No.: US 11,419,764 B2
(45) Date of Patent: Aug. 23, 2022

(54) OPHTHALMOLOGICAL TREATMENT APPARATUS

(71) Applicant: ZIEMER OPHTHALMIC SYSTEMS AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 710 days.

(21) Appl. No.: 16/301,269

(22) PCT Filed: May 3, 2017

(86) PCT No.: PCT/EP2017/060486
§ 371 (c)(1),
(2) Date: Nov. 13, 2018

(87) PCT Pub. No.: WO2017/198462
PCT Pub. Date: Nov. 23, 2017

(65) Prior Publication Data
US 2020/0315847 A1 Oct. 8, 2020

(30) Foreign Application Priority Data
May 17, 2016 (EP) .................................. 16169856

(51) Int. Cl.
*A61F 9/008* (2006.01)
*G16H 20/40* (2018.01)

(52) U.S. Cl.
CPC ......... *A61F 9/00827* (2013.01); *G16H 20/40* (2018.01); *A61F 2009/00853* (2013.01);
(Continued)

(58) Field of Classification Search
CPC ........ A61F 9/00827; A61F 2009/00853; A61F 2009/00872; A61F 2009/00878; A61F 2009/00897; G16H 20/40
See application file for complete search history.

(56) References Cited

U.S. PATENT DOCUMENTS

| 5,531,753 A | 7/1996 | Oliveira |
| 2007/0208325 A1* | 9/2007 | Kurtz .................. A61F 9/00831 606/4 |

(Continued)

FOREIGN PATENT DOCUMENTS

| EP | 1 731 120 A1 | 12/2006 |
| EP | 2853247 A1 | 4/2015 |

(Continued)

OTHER PUBLICATIONS

Jul. 12, 2017—International Search Report—App PCT/EP2017/060486.
Nov. 8, 2016—(EP) Search Report—App 16169856.8.

*Primary Examiner* — Nathan J Jenness
(74) *Attorney, Agent, or Firm* — Banner & Witcoff, Ltd.

(57) ABSTRACT

Disclosed is an ophthalmological treatment apparatus for modifying a shape of a corneal surface of a human eye. The apparatus includes a surgical laser device for implementing tissue cuts. The apparatus further includes a computerized control device in operative coupling with the surgical laser device, the control device being designed to control the laser device to implement tissue cuts according to a cut geometry with a primary tissue cut and a secondary tissue cut, wherein the primary tissue cut is a relief cut and extends into the depth of the corneal eye tissue, and wherein the secondary tissue cut lies within the corneal eye tissue, such that the secondary tissue cut adds to the relieving effect of the primary tissue cut.

14 Claims, 4 Drawing Sheets

(52) U.S. Cl.
CPC ............... *A61F 2009/00872* (2013.01); *A61F 2009/00878* (2013.01); *A61F 2009/00897* (2013.01)

(56) References Cited

U.S. PATENT DOCUMENTS

| | | | | |
|---|---|---|---|---|
| 2008/0058777 | A1* | 3/2008 | Kurtz | A61F 9/008 606/4 |
| 2012/0083775 | A1* | 4/2012 | Donitzky | A61F 9/00804 606/5 |
| 2012/0296321 | A1 | 11/2012 | Frey et al. | |
| 2013/0324984 | A1* | 12/2013 | Seiler | A61F 9/00831 606/5 |
| 2014/0058365 | A1* | 2/2014 | Bille | A61F 9/00827 606/5 |
| 2015/0374549 | A1 | 12/2015 | Scott | |

FOREIGN PATENT DOCUMENTS

| | | |
|---|---|---|
| WO | 2008/014419 A2 | 1/2008 |
| WO | 2008/030699 A2 | 3/2008 |
| WO | 2009/158723 A2 | 12/2009 |
| WO | 2012/134979 A1 | 10/2012 |

\* cited by examiner

OPHTHALMOLOGICAL TREATMENT APPARATUS

CROSS-REFERENCE TO RELATED APPLICATIONS

The present application is a U.S. National Phase filing of International Application No. PCT/EP2017/060486, filed on May 3, 2017, and claiming priority to EP Patent Application No. 16169856.8 filed May 17, 2016. The present application claims priority to and the benefit of all the above-identified applications, which are all incorporated by reference herein in their entireties.

TECHNICAL FIELD

The present invention lies in the field of ophthalmologic surgery, in particular refractive laser surgery, as well as corresponding methods.

BACKGROUND

Prior Art

In the field of ophthalmologic surgery, laser-based systems and methods are increasingly applied where eye tissue, e. g. corneal tissue, of a patient's eye is surgically treated and for example cut by way of controlled and focused laser radiation, rather than with a classical (diamond) scalpel. The corresponding technics is referred to as laser surgery.

A class of ophthalmologic surgical procedures is based on implementing well-defined incisions into the corneal tissue, classically with a scalpel (also named keratome). The incisions serve as relief cuts and result, under influence of the intraocular pressure, in a desired deformation of the cornea, thereby modifying its refractive power. Corresponding surgical technics are known, for example, as radial keratotomy RK or, for example, as arcuate keratotomy AK (also referred to as arcuate incisions, arcuate cuts or astigmatic keratotomy) or limbal relaxing incisions, LRI.

US 2012/0296321 A1 discloses a method for correcting astigmatism by implementing paired arcuate laser generated incisions into the corneal tissue. U.S. Pat. No. 5,531,753 discloses a surgical astigmatism correction using a mechanical instrument.

SUMMARY OF DISCLOSURE

A drawback of implementing relief cuts into the corneal tissue according to the state of the art is the fact that the required cuts are comparatively deep, generally having an incision depth of 70% to 90% of the cornea thickness (thickness of the corneal tissue), which is accordingly severely weakened.

It is an overall objective of the present invention to improve the state of the art regarding refractive surgery by modifying of the cornea surface. Favorably, apparatuses and methods are provided that allow to achieve the desired optical effect with less weakening of the cornea structure and to provide a new parameter of adjustment. Further favorably, apparatuses and methods are provided that allow to modify the cornea surface, that are flexible and allow an adaption to a large variety of medical situations and required cornea surface modifications.

In a general way, the overall objective is achieved by way of the subject matter of the independent claims. Exemplary and particularly favorable embodiments are further defined by way of the dependent claims as well as the overall disclosure of the present document.

According to an aspect, the overall objective is achieved by an ophthalmological treatment apparatus for modifying a shape of a cornea surface of a human eye. The ophthalmologic treatment apparatus includes a surgical laser device for implementing tissue cuts. The ophthalmologic treatment apparatus further includes a computerized control device in operative coupling with the surgical laser device. The control device is designed to control the laser device to implement tissue cuts according to a cut geometry with a primary tissue cut and a secondary tissue cut. The primary tissue cut is a relief cut and extends into the depth of the tissue. The secondary tissue cut lies within the tissue, such that the secondary tissue cut adds to the relieving effect of the primary tissue cut. The primary tissue cut and the secondary tissue cut are each defined by a corresponding spatial cut surface along which the tissue is separated.

Implementing the primary tissue cut and the secondary tissue cut may be carried out in combination and in a common surgical procedure. They may, however, also implemented separately and in separate surgical procedures.

The tissue into which the primary tissue cut and the secondary tissue cut are implemented is eye tissue, in particular corneal tissue, limbal tissue or a combination thereof. For exemplary purposes, the description in the document mainly deals with cuts into the corneal tissue, without, however, excluding limbal tissue.

The present invention is based on biomechanical considerations regarding the eye tissue. Without any tissue cuts being implemented, the tissue is tensioned by the intraocular pressure. The intraocular pressure is associated with outward directed forces that are directed from the aqueous humor towards the periphery, thereby straining and stressing the tissue with additional deformation. If a tissue cut is implemented that extends, for example, from the anterior tissue surface into the corneal tissue and has an orientation with a component perpendicular to the stresses mentioned before, such tissue cut results in a stress peak respectively an area of increased stress at the ground of the tissue cut inside the tissue, the stress peak causing an additional deformation. These considerations form the basis for corneal or limbal incision procedures, such as arcuate keratotomy, as known per se and classically carried out using a scalpel.

In accordance with the present invention, the primary tissue cut is a tissue cut of the before-mentioned type. According to a basic embodiment of the present invention, a secondary tissue cute is implemented that extends traverse to the primary tissue cut and inside the tissue. If such traverse secondary tissue cut meets with the ground of the primary tissue cut or is, alternatively, sufficiently close to the primary tissue cut, it is found that the area of increased stress is enlarged, thereby favorably enlarging the deformation resulting from the primary tissue cut. In embodiment, the secondary tissue cut is arranged such that it extends in the tissue an area of increased mechanical stress which results from the primary tissue cut, thereby increasing a corneal tissue deformation resulting from the primary-tissue cut. To achieve this effect, some width (measured as tangential distance between the inner edge and the outer edge) is required for the secondary tissue cut. Typically, the width is at least 10% of the uncut stroma of the primary tissue cut, respectively at least 10% of the distance from the ground of the primary tissue cut to the posterior corneal surface.

For a refractive surgery based on known corneal incision procedures, the depth of the cut or incision (primary tissue cut in context of the present invention), an incision depth of at least 70% of the corneal tissue thickness is typically required in order to achieve a significant effect at all, with up to 90% being typically required. For a cut geometry in accordance with the present invention, in contrast, the depth of the primary tissue cut may be in a range of 50% to 70% of the tissue thickness as a maximum. Thereby, the undesired weakening that inevitably results from the tissue cuts, is reduced. Further, by enlarging the area of increased stress, the absolute stress and stress gradients are reduced. As a consequence, the stress-strain relation is linear or at least close-to-linear, resulting in a generally less critical behavior of the tissue and in particular a less critical adjustment of the cut geometry parameters as compared to known corneal incision procedures, e. g. classical arcuate keratotomy.

The secondary tissue cut may be implemented as a continuous single cut. This type of embodiment is generally assumed in the following. Alternatively, it may be split along its length into two or more secondary sub cuts that are separated by tissue bridges.

The surgical laser device may, for example, have a base device with a laser light source for generating laser pulses and an application head with a projection lens which is coupled to the patient eye for treatment purposes and in particular implementing tissue cuts into the eye tissue. The application head can be movably connected to the base device, for example by way of an articulated arm, wherein the articulated arm may simultaneously serve for optical beam guidance from the laser light source to the application head. By way of example, a corresponding arrangement is disclosed in EP 1731120. Moreover, there are devices in which the application head is integrated into the base device or in which other device arrangements are provided and which may be used as well. Integrations into microscopes or attachments to microscopes are also proposed.

The computerized control device may be designed based on general-purpose computing equipment, such as one or more personal computers (PCs) or workstations, and includes components such as one or more microcontrollers and/or microprocessors, volatile and non-volatile memory, a user interface with components such monitors, a keyboard, mouse, trackball, or the like. Operation of the ophthalmologic treatment apparatus and in particular of the surgical laser device is favorably controlled via corresponding software code that runs on the one or more microcontrollers and/or microcomputers and is stored in volatile and/or non-volatile memory. The control device further includes interface circuitry for operative coupling with the surgical laser device and may further include interface circuitry for coupling with external devices, such as external computing devices, a local area network (LAN), the internet, or the like. The control device may, fully or partly, be integral with the base device of a surgical laser device as explained before.

In an embodiment, the surgical laser device includes a femtosecond laser source. A femtosecond lase is particularly favorable in that it allows to implement the tissue cut with high precision and reproducibility. Nano or picosecond laser in the UV range may be used in alternative embodiments.

In an embodiment, the primary tissue cut is an arcuate cut. The arc of the arcuate cut is typically centered with respect to a symmetry axis of the eye. The radial distance from a symmetry axis (e.g. geometrical axis, optical axis, visual axis), the incision depth and the arc length may be selected patient-specific in dependence of the required tissue deformation to be achieved. For this type of embodiment, the primary tissue cut is generally similar to the incision of arcuate keratotomy.

For the primary tissue cut being an arcuate cut of circumferential angle and diameter (as measured from the cornea center respectively the optical axis), the secondary tissue cut may, for example, have an inner arcuate limitation and an outer arcuate limitation that are symmetric to the arc of the primary tissue cut, with the arc of the inner arcuate limitation having a smaller diameter and the arc of the outer arcuate limitation having a larger diameter than the arc of the arcuate primary tissue cut. The secondary tissue cut may be flush with the primary tissue cut, with the arc of the outer arcuate limitation, the arc of the inner arcuate limitation, and the arc of the primary tissue cut having identical circumferential angles. Alternatively, the primary tissue cut may project beyond the secondary tissue cut, or vice versa.

In variants, the secondary tissue cut is unsymmetrical with respect to the primary tissue cut. In further variants, arcuate tissue cuts are replaced respectively approximated by a planar tissue cut or a number of planar adjacent planar tissue cuts. For planar tissue cuts, the arcs are replaced by straight lines respectively polygonal lines.

In an embodiment, the primary tissue cut extends to an outer tissue surface. For this type of embodiment, the primary tissue cut is an incision that extends from the outer or anterior tissue surface (anterior cornea surface and/or limbal surface) into the eye tissue. In contrast to the primary tissue cut, the secondary tissue cut is generally surface incision-free and fully extends within the eye tissue and not to the outer surface. In contrast to an incision that may in principle—however with reduced accuracy and reproducibility—also be implemented using a scalpel, laser surgery is required for incision-free cuts.

In an alternative embodiment, also the primary tissue cut extends fully within the tissue without extending to the surface. Since the epithelium is not cut, the inherent infection risk is significantly reduced for this type of embodiment.

In an embodiment, the primary tissue cut and the secondary tissue cut are spatially curved. The primary tissue cut may especially be arcuate as mentioned before in a top view, i. e. in a viewing direction parallel to the symmetry axis of the eye. The depth of first tissue cut may be constant or vary along its lengths.

The width of the secondary tissue cut (measured as radial distance between the inner edge and the outer edge) may further be constant or vary along the length of the secondary tissue cut continuously or discretely.

In an embodiment, the primary tissue cut and the secondary tissue cut meet or intersect along a joint line. This type of embodiment generally results in a maximum combined effect of the primary and secondary tissue cut and in particular a maximum adding of the secondary tissue cut to the relieving effect to the primary tissue cut. The joint line lies within the eye tissue.

The primary tissue cut and the secondary tissue cut meeting along the joint line means that the primary tissue cut and the secondary tissue cut touch each other along the joint line, but the primary tissue cut does not extend beyond the secondary tissue cut in the depth direction of the tissue. With other words, the ground of the primary tissue cut lies in the surface of the secondary tissue cut. Such cut geometry is generally favorable for achieving the desired relieving effect with minimum tissue weakening. There is, however, some risk of undesired tissue bridges remaining between the primary tissue cut and the secondary tissue cut.

The primary tissue cut and the secondary tissue cut alternatively intersecting align the joint line (intersection line) means that the primary tissue cut extends beyond the secondary tissue cut into the depth of the corneal tissue. With other words, the ground of the primary tissue cut lies deeper in the tissue as compared to the joint line. Such cut geometry may be chosen in order to avoid undesired tissue bridges. If a cut geometry with meeting respectively touching primary and secondary tissue cut is initially chosen, it may also be modified into a cut geometry with intersecting primary and secondary tissue cut in a subsequent laser surgical procedure if undesired tissue bridges are found to be remaining.

In an embodiment, the primary tissue cut and the secondary tissue cut are separated by a tissue bridge. For such alternative type of embodiment, the primary tissue cut and the secondary tissue cut are purposely separated from each other by the tissue bridge. The tissue bridge, however, is sufficiently narrow to allow the secondary tissue cut to add to the relieving effect as explained before. If, subsequent to the surgical procedure, the obtained tissue deformation is found to be insufficient, the tissue bridge may be fully or partly removed by way of a subsequent manual or laser surgical procedure, thereby increasing the corneal tissue deformation. The secondary tissue cut may be radially symmetrical or unsymmetrical to the primary tissue cut and may radially extend from the primary tissue cut towards the center and the symmetry axis, and/or towards the periphery.

In an embodiment, the secondary tissue cut extends in a constant distance from a posterior corneal surface. Typically, the secondary tissue cut extends in a constant depth of the tissue. In a modification, the secondary tissue cut includes a central region that extends in a constant distance from the posterior corneal tissue surface, and an adjoining peripheral region that extends from the central region towards the outer cornea surface. The peripheral region may especially extend in an area of the edges of the secondary tissue cut. Such latter type of embodiment favorably avoids stress peaks along the periphery of the secondary tissue cuts, which result in a largely non-linear material behavior, in particular stress-strain relation.

In embodiment, the primary tissue cut and the secondary tissue cut are perpendicular with respect to each other. More specifically, a reference plane exists for this type of embodiment such that an angle that can be determined between the primary tissue cut and the secondary tissue cut in the reference plane is or is close to a right angle. Alternatively, the primary tissue cut and the secondary tissue cut may be inclined with respect to each other which is favorable in order to avoid a gaping wound.

In an embodiment, the cut geometry includes, in addition to the primary tissue cut, a further primary tissue cut, wherein the further primary tissue cut extends into the depth of the tissue. The primary tissue cut and the further primary tissue cut may especially be symmetric relative to the secondary tissue cut. Such type of embodiment with a further primary tissue cut is favorable regarding wound closure, respectively in order to avoid gaping wounds.

In an embodiment, the cut geometry includes, in addition to the secondary tissue cut, a further secondary tissue cut. The further secondary tissue cut lies within the tissue. The secondary tissue cut and the further secondary tissue cut are spaced apart from each other along the corneal tissue depth. The primary tissue cut may especially extend between the secondary tissue cut and the further secondary tissue cut. For this type of embodiment, the inherent infection risk is reduced, while the tissue deformation is increased.

In an embodiment, the control device is designed to control the surgical laser device to implement the secondary tissue cut prior to implementing the primary tissue cut. The secondary tissue cut does, as such, not result in a substantial tissue deformation, but only combination with the primary tissue cut. This type of embodiment accordingly allows to implement the secondary tissue cut in the original state of the tissue without needing to consider the deformation resulting from the cuts.

In an embodiment, the control device is designed to control the surgical laser device to start implementing the primary tissue cut at a starting position within the tissue and advance towards the outer corneal tissue surface. The maximum tissue deformation occurs when the primary tissue cut meets the outer or anterior surface. Starting with implementing the primary tissue cut within the tissue—typically in the greatest depth that forms the ground of the primary tissue cut—accordingly allows to implement most of the primary tissue without or little tissue deformation.

In an embodiment, the control device includes or is operatively coupled to a cut geometry template storage, the cut geometry template storage storing a number of pre-defined cut geometry templates, and is designed to select the cut geometry as one of the cut geometry templates.

The cut geometry template storage in particular stores cut geometries in accordance with the present invention in a volatile and/or non-volatile memory and a user-selection by an operator of a suited cut geometry is made via a user interface.

In an embodiment, the control device is designed to receive at least one patient-specific cut geometry parameter and to compute the cut geometry by applying the at least one patient-specific cut geometry parameter to a stored generic cut geometry template.

The generic cut geometry template may, for example, be a cut geometry template that is selected from a number of stored cut geometry templates as explained before. Typical patient-specific cut geometry parameters in a basic cut geometry are the arc length and/or the radius and/or the depth of the primary tissue cut, and the width of the secondary tissue cut, and an axis (e.g. geometrical axis, optical axis, visual axis) with respect to which the tissue cuts are centered. Further optional patient-specific cut-geometry parameters of special cut geometries are discussed further below in the context of exemplary embodiments.

Entry of patient-specific cut geometry parameters may be done manually by an operator via user interface, such as keyboard, mouse or trackball.

In an embodiment, the control device includes or is coupled to an ophthalmologic measurement device, such as a corneal topographer, a corneal tomographer and/or a camera device that provide suited medical images of the patient eyes on a computer monitor or the like. A cut geometry, e. g. according to a cut-geometry template as explained, may be shown superimposed onto one or more medical images and may optionally be modified and/or parameterized via a graphical user interface as generally known in the art.

Optionally, parameters or parameter sets for desired corneal tissue modifications may be stored in a database and be selected by a user and/or selected and applied or proposed automatically by the control device, generally similar to nomograms that are presently used e. g. for selecting the parameters of arcuate tissue cuts in accordance with the state of the art.

According to a further aspect, the overall objective is achieved by a method for modifying a cornea surface of a human eye. The method includes controlling the surgical laser device to implement tissue cuts according to a cut geometry, wherein the primary tissue cut is a relief cut and extends into the depth of the tissue and the secondary tissue cut lies within the tissue, such that the secondary tissue cut adds to the relieving effect of the primary tissue cut.

In particular embodiments, the cut geometry may be a cut geometry according to any embodiment as described above and/or further below in the context of exemplary embodiments. Further aspects of particular embodiments and variants of a method in accordance with the present disclosure are also discussed above and/or further below.

According to a further aspect, the overall objective is achieved by a computer program product including a non-transient computer readable medium having stored therein computer program code. The computer program code is configured to direct a processor of a computerized control device in operative coupling with a surgical laser device, to control the laser device to implement tissue cuts according to a cut geometry with a primary tissue cut and a secondary tissue cut. The primary tissue cut is a relief cut and extends into the depth of the tissue. The secondary tissue cut lies within the tissue, such that the secondary tissue cut adds to the relieving effect of the primary tissue cut.

According to a further aspect, the overall objective is achieved by a further ophthalmological treatment apparatus for modifying a shape of a corneal surface of a human eye. The ophthalmologic treatment apparatus includes a surgical laser device for implementing tissue cuts. The ophthalmologic treatment apparatus further includes a computerized control device in operative coupling with the surgical laser device. The control device is designed to receive cut information of a primary tissue cut. The primary tissue cut is a relief cut and extends into the depth of the tissue. The control device is further designed to control the surgical laser device to implement a secondary tissue cut. The secondary tissue cut lies within the tissue, such that the secondary tissue cut adds to the relieving effect of the primary tissue cut.

The primary tissue cut is defined by the received cut information that in particular comprises information regarding the cut geometry and the position of the primary tissue cut in the tissue. The cut geometry information may be received, for example, via a data interface from a further device or on a data carrier, such as a CD-ROM, or may be acquired by an ophthalmologic measurement device in operative coupling with the control device.

According to a further aspect, the overall objective is achieved by a further method for modifying a cornea surface of a human eye. The method includes receiving cut information of a primary tissue cut. The primary tissue cut is a relief cut and extends into the depth of the tissue. The method further includes controlling a surgical laser device to implement a secondary tissue cut. The secondary tissue cut lies within the tissue, such that the secondary tissue cut adds to the relieving effect of the primary tissue cut.

According to a further aspect, the overall objective is achieved by a further computer program product including a non-transient computer readable medium having stored therein computer program code. The computer program code is configured to direct a processor of a computerized control device in operative coupling with a surgical laser device to receive cut information of a primary tissue cut, wherein the primary tissue cut is a relief cut and extends into the depth of the tissue. The computer program code is further configured to direct the control device to control the surgical device to implement a secondary tissue cut, wherein the secondary tissue cut lies within the tissue, such that the secondary tissue cut adds to the relieving effect of the primary tissue cut.

This type of apparatus, method computer program product may be favorably used in situations where a relief cut, for example an arcuate cut as generally known, is already present and further visual correction is required. In combination, the primary tissue cut and the secondary tissue cut establish a cut geometry as explained before. Also, the secondary tissue cut may intentionally be implemented in a second surgical procedure subsequent to implementing the primary tissue cut for medical reasons.

Exemplary and favorable embodiments of the before described ophthalmologic treatment apparatus, method for modifying a cornea surface or computer program product also define corresponding embodiments of the further described ophthalmologic treatment apparatus, method for modifying a cornea surface, or computer program product.

Computer code may especially be configured to direct a processor of a computerized control device of an ophthalmologic treatment apparatus to operate according to an embodiment of an ophthalmologic treatment apparatus as explained before and/or further below in the context of exemplary embodiments. The term "processor" is to be understood as a microprocessor, microcontroller or a combination of a number of microprocessors and/or microcontrollers.

BRIEF DESCRIPTION OF THE FIGURES

FIG. 4-4m illustrate exemplary embodiments of cut geometries in a sectional view;

EXEMPLARY EMBODIMENTS

Figure 1:
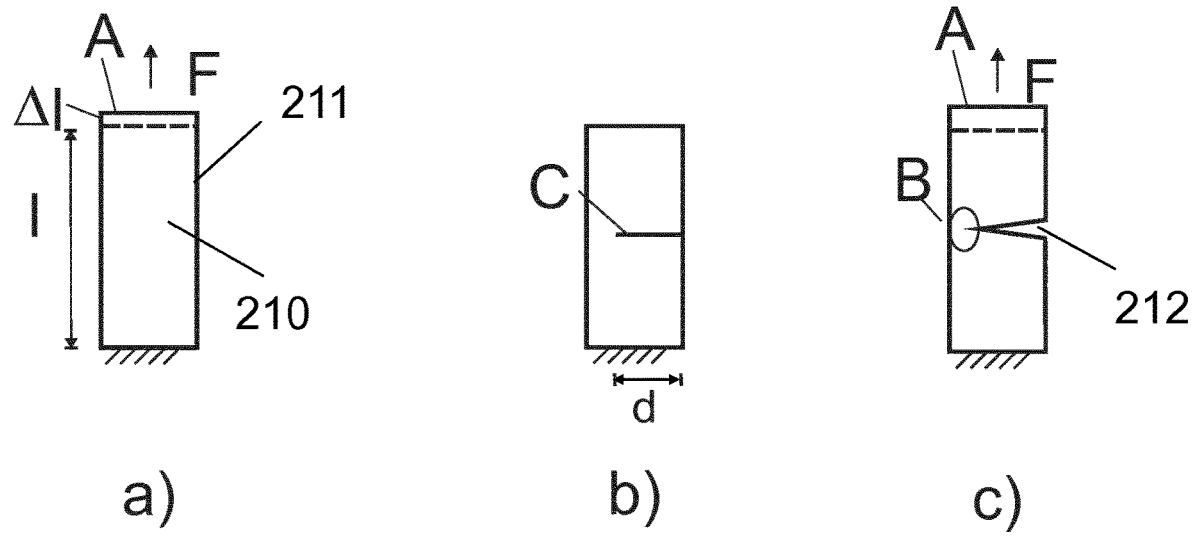
FIG. 1a-1c illustrate the biomechanical principle of a relief cut into the corneal tissue.

Where, with reference to the figures, directional terms such as "top", "bottom"; "left", "right", "above", or "below" are used, such terms are only intended to guide the reader's view and to improve the understanding of the figures. They are not meant to imply any particular directions and/or relative positions during application, unless stated differently in a specific context.

In the following, reference is first made to FIG. 1a-FIG. 1c and FIG. 2a-FIG. 2b, illustrating the underlying biomechanical principle of the present invention in a simplified one-dimensional model.

Further in the following description, it is assumed that the eye tissue into which the tissue cuts are implemented is corneal tissue. The considerations and examples, however, also hold true for limbal tissue in an analogue way.

It is to be understood that the corneal tissue, the intracorneal tissue stress and the effect from implementing tissue cuts into or within the corneal tissue are three-dimensional. This three-dimensional real world situation may be approximated with good accuracy by a two-dimensional membrane strain model. Since the main effect of the tension is tangential to the cornea surface and perpendicular to the tissue cut projection, it may, in particular for illustrative purposes, be further simplified to a one-dimensional model. This approach is used in the following description.

FIG. 1a shows a rod of length l as one-dimensional model of the corneal tissue 210, with the anterior (outer) cornea surface being referenced 211. Assuming one end (bottom end, not referenced) of the rod to be fixed, the rod is strained with a displacement Δl under influence of a force F which results from the intra-ocular pressure. Accordingly, the top end A of the rod is displaced by Δl. Stress (Force F divided by the cross-section of the rod) and strain (Δl/l) are constant across the rod. In FIG. 1b, a tissue cut C is implemented that extends from the anterior (outer) cornea surface and into the corneal tissue, traverse to the direction of the force F. The tissue cut C has a depth d as measured from the cornea surface 211 to the (not reference) ground of the cut inside the corneal tissue 210. As best visible in FIG. 1c, the tissue cut C results in a zone B of increased stress and strain at the bottom of the tissue cut C, resulting in a gap 212 that extends from the cornea surface 211 into the corneal tissue 210, and an increased displacement of the corneal tissue 210 (see position of end A in FIG. 1c as compared to FIG. 1a). To this extend, FIG. 1a-FIG. 1c illustrate the situation of a corneal incision procedure as generally known in the art, with the cut C being, e. g., an arcuate incision for the case of arcuate keratotomy.

In accordance with the present invention, an additional tissue cut C' may be implemented in addition to the tissue cut C as primary tissue cut, as shown in FIG. 2a. The secondary tissue cut C' extends fully inside the corneal tissue 210 and is traverse to the primary tissue cut C. As best visible in FIG. 2b, the secondary tissue cut C' results in a larger zone B' of increased stress, which in turn results in a wider gap 212' and an increased displacement as compared to a situation with only the primary tissue cut C being implemented (see FIG. 2b as compared to FIG. 1c). With s being the width of the secondary tissue cut as indicated, the effect of the secondary tissue cut C' increases with s, thereby providing a new additional parameter that may be selected or adjusted to achieve the desired tissue deformation.

Figure 3:
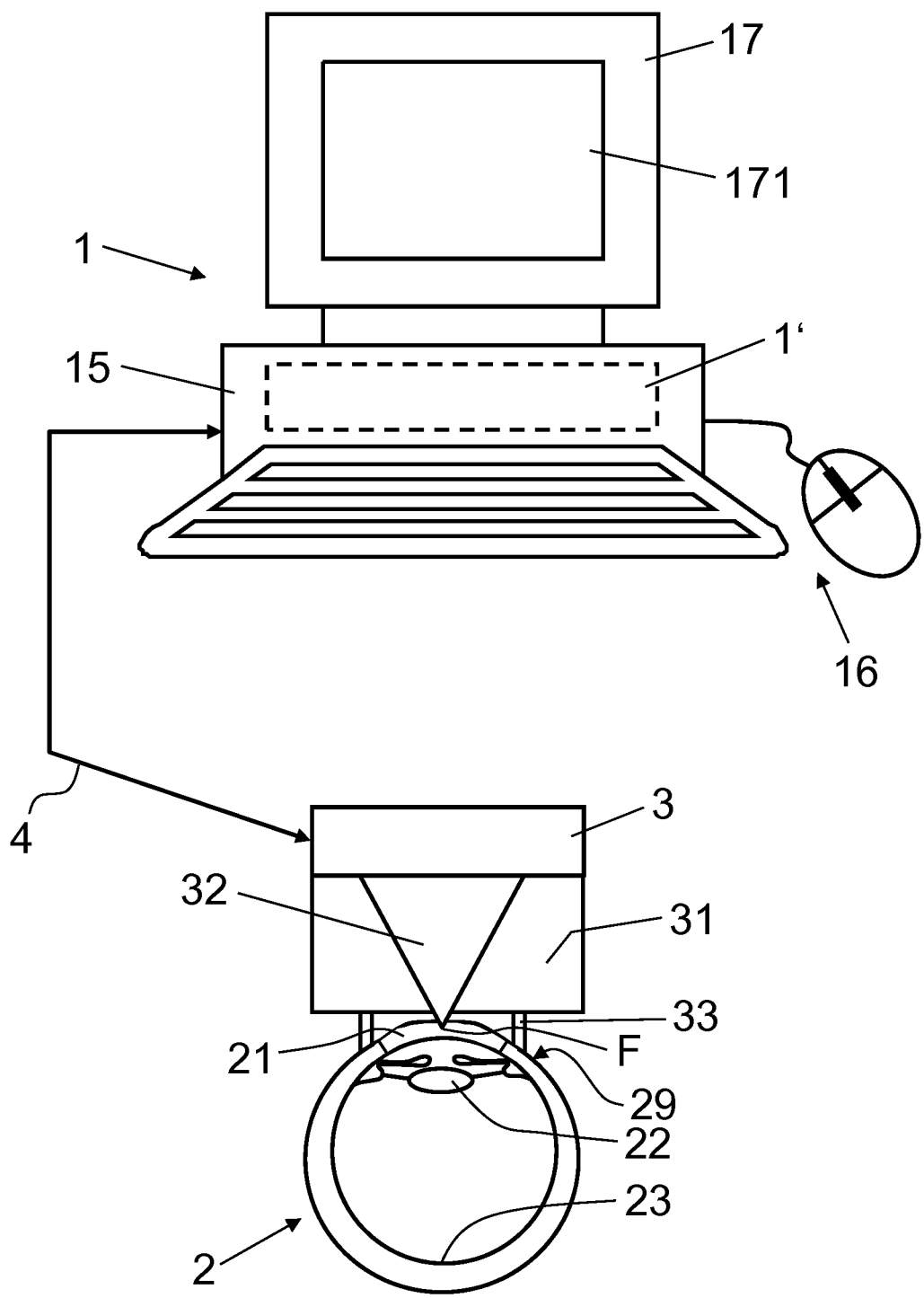
FIG. 3 show an ophthalmologic treatment apparatus in a schematic view.

In the following, reference is additionally made to FIG. 3. FIG. 3 shows an exemplary embodiment of an ophthalmologic treatment apparatus 1, 3, in accordance with the present disclosure and in interaction with a human eye (patient eye) 2 in a schematic view.

For the human eye 2, the cornea 21, the lens 22, the retina 23 and the sclera 29 are shown. Further, the limbus (not separately referenced) is present as transition area between the cornea 21 and the sclera 29. Some cuts or incision, in particular limbal relaxing incisions, LRI, are made in the limbal tissue. A direction from "outer" towards "inner" is a direction from the outer surface of the cornea 21 and the sclera 29 towards the retina 23.

The ophthalmologic treatment apparatus comprises the control device 1 and the surgical laser device 3 that is exemplarily based on a femtosecond laser source in operative coupling with a projection lens that is part of an application head (components as scanners and beam delivery and shaping optics are not separately shown). From the laser device 3 respective its projection lens, laser radiation is emitted and focused onto a point of the corneal tissue 210 (indicated by radiation cone 32). In a situation of use, the surgical laser device 3 is coupled to the eye 2 via a patient interface 31 that is typically designed for one-way use and couples with the surgical laser device 3 respectively its application head via releasable mechanical coupling and for coupling with the eye 2 respective its sclera 29 and/or cornea 21 via a suction ring 33. Coupling is not mandatory if the laser can compensate for eye movement or is fast enough. The patient interface 31 may be designed to deform the eye surface to a desired shape for the surgical procedure, e. g. planar, spherical or aspherical shape with an applanation-type coupling and a transparent contact body.

Alternatively, the patient interface 31 may be designed to couple with the eye 2, in particular the cornea 21, via a contact liquid, e. g. saline solution, substantially without causing deformation. An exemplary patient interface is disclosed in the EP2853247.

The control device 1 is exemplarily shown as being based on a general purpose computing device 15, such as a PC or workstation, in operative coupling with a user interface that includes an input unit 16 (shown with a keyboard and a mouse for exemplary purposes) and an output unit 17 (exemplarily shown as computer monitor with an image area 171). Other devices for the input unit 16 and/or the output unit 17 may be used as well. For example, the input unit 16, may include a track ball and/or a touch pad. The output unit 17 may, for example, be or include a beamer or glasses with integrated display, to be worn by an operator.

The control device 1 includes a number of functional modules 1', which include interface circuitry for coupling with the surgical laser device 3 via an (typically electrical) operative coupling 4. The control device 1 further includes one or more processors, e. g. microprocessors and/or microcontrollers, for controlling operation of the control device 1 and the ophthalmologic treatment apparatus as a whole in accordance with corresponding program code. The control device 1 further includes volatile and/or non-volatile memory that stores program code and/or data.

In FIG. 3, the control device is shown as a compact unit. The control device 1 may, however, also be distributed between a number of computing devices, each with particular functional units 1'. The computing devices may be coupled via data interfaces such as a LAN network or USB connection for data transfer and/or between which data may be transferred via physical media, such as CD-ROMS, DVDs, magnetic storage discs, or the like. Further, the control device 1 may be fully or partly integrated with the surgical laser device 3.

Figure 2:
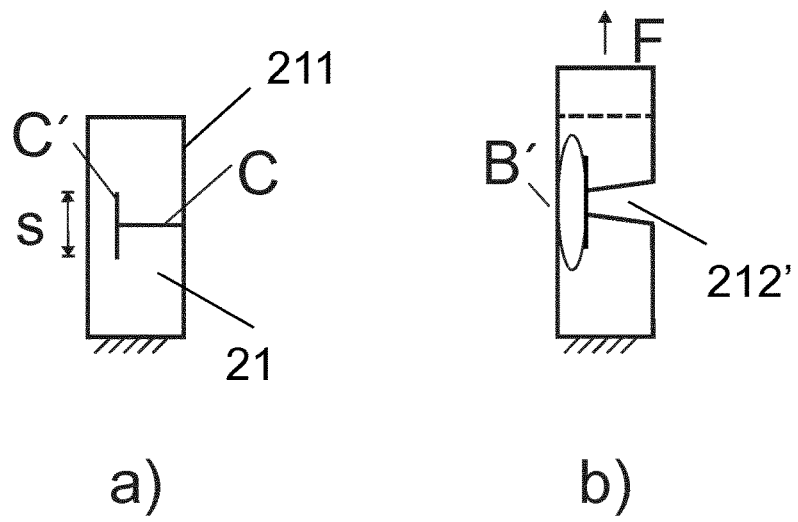
FIG. 2a-2b illustrate the principle of a cut geometry with a primary tissue cut and a secondary tissue cut.

In the following, reference is additionally made to FIG. 4a-FIG. 4m, showing a variety of exemplary cut geometries in accordance with the present invention in a schematic one-dimensional view, generally similar to the view of before-discussed figures FIG. 1, FIG. 2. The arrow "t" indicates a direction tangential respectively parallel to the cornea surface 211 and pointing radially from the center of the cornea 21 towards the sclera 29. A direction traverse to the cornea surface 211 into the corneal tissue is referred to as depth direction (not referenced) and a distance from the cornea surface as depth. The figures may be considered as cross sectional views of the corneal tissue in the area of the tissue cuts. Generally, geometrical relations such as parallel, perpendicular or mirrored refer to the view as shown.

Figure 4:
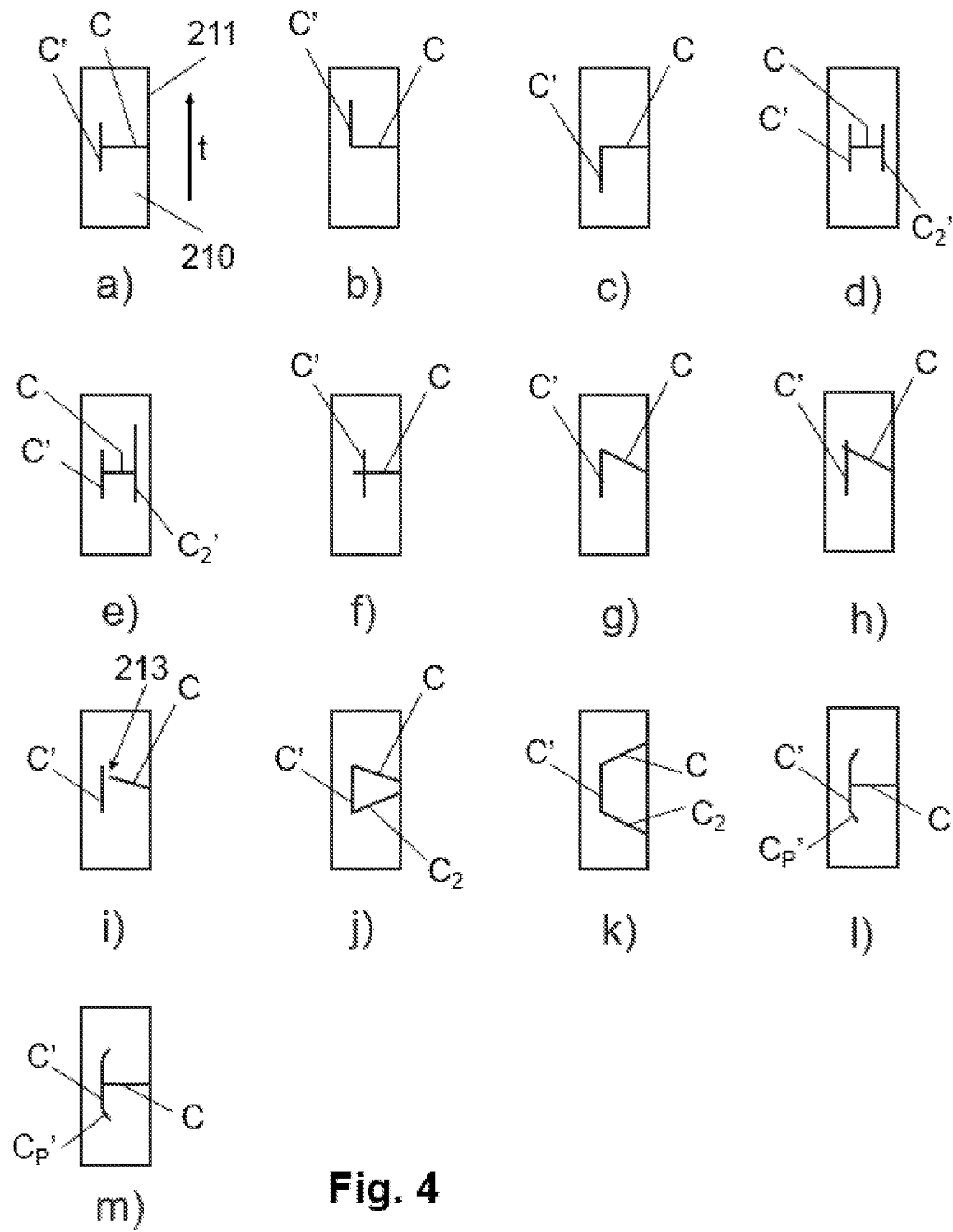

FIG. 4a shows a basic embodiment of a cut geometry with the secondary tissue cut being C' being tangentially symmetric with respect to the primary tissue cut C and perpendicular to the primary tissue cut C. The primary tissue cut C and the secondary tissue cut C' meet along a joint line, resulting in an overall T-shaped cut geometry in the sectional view. FIG. 4a generally corresponds to FIG. 2a as discussed before.

The cut geometry as shown in FIG. 4b is similar to the cut geometry as shown in FIG. 4a. The secondary tissue cut C', however is tangentially displaced with respect to the primary tissue cut C. In this example, the secondary tissue cut is displaced by half of the cut width s (see FIG. 2a) as compared to FIG. 4a, resulting in an L-shaped cut geometry in the cross sectional view. Alternatively, the secondary tissue cut C' may be displaced by less or somewhat more than half of the cut width. The amount of displacement is a cut geometry parameter that may be selected by a user or automatically.

The cut geometry as shown in FIG. 4c is similar to the cut geometry as shown in FIG. 4b. The secondary tissue cut C', however is radially displaced with respect to the primary tissue cut C into the opposite direction as compared to FIG. 4b. The cross sectional cut geometry of FIG. 4c may accordingly be obtained by mirroring the secondary tissue cut C' with respect to the primary tissue cut C. Similarly, the cut geometries shown and discussed in the following examples may be mirrored in an analogue way.

For the cut geometry as shown in FIG. 4d, a secondary tissue cut C' and a further secondary tissue cut $C_2$' are present. The secondary tissue cut C' and the further secondary tissue cut $C_2$' are spaced apart from each other in the depth direction, with the distance being bridged by the primary tissue cut C, such that one end of the primary tissue cut C meets with the secondary tissue cut C' and the other end of the primary tissue cut C meets with the further secondary tissue cut $C_2$' along corresponding joint lines. The cross sectional tissue cut geometry is accordingly H-shaped. In contrast to the examples of FIG. 4a-FIG. 4c and FIG. 4f-FIG. 4m, the primary tissue cut does not extend to the anterior (outer) cornea surface 211, but all tissue cuts lie fully within the corneal tissue 210.

The cut geometry as shown in FIG. 4e is similar to the cut geometry as shown in FIG. 4d. The further secondary tissue cut $C_2$', however is tangentially displaced with respect to the primary tissue cut C. It is noted that in cut geometries with a secondary tissue cut C' and a further secondary tissue cut $C_2$', the naming as secondary tissue cut C' respectively further secondary tissue cut $C_2$' is generally arbitrary and may be interchanged.

The cut geometry as shown in FIG. 4f is similar to the cut geometry as shown in FIG. 4a. The primary tissue cut C, however, extends deeper into the corneal tissue 210 and beyond the secondary tissue cut C', resulting in the primary tissue cut C and the secondary tissue cut C' intersecting rather than meeting. The distance by which the primary tissue cut C extends beyond the secondary tissue cut C' may be a further cut geometry parameter. As explained before, such configuration may be favorably used in order to avoid undesired tissue bridges.

The cut geometry as shown in FIG. 4g is similar to the cut geometry as shown in FIG. 4a. The primary tissue cut C, however, is inclined rather than perpendicular with respect to the cornea surface 211, resulting in the primary tissue cut C and the secondary tissue cut C' meeting with an angle different from perpendicular. As explained before, such configuration may be favorably used in order to avoid gaping wounds. The angle of inclination may be a further cut geometry parameter. The cut geometry is such that the joint line is defined by an edge of the secondary tissue cut C' and the ground of the primary tissue cut C.

The cut geometry as shown in FIG. 4h is similar to the cut geometry as shown in FIG. 4g. However, the ground of the primary tissue cut C does not meet with an edge of the secondary tissue cut C', but is somewhat inwardly displaced, resulting in the secondary tissue cut C' extending beyond the joint line in tangential direction. Further, the primary tissue cut C extends beyond the secondary tissue cut C' and deeper into the corneal tissue 210. Similar to the cut geometry of FIG. 4f, as discussed before, such arrangement avoids gaping wounds and tissue bridges.

The cut geometry as shown in FIG. 4i is similar to the cut geometry as shown in FIG. 4g. The primary tissue cut C, however, does not extend to the secondary tissue cut C', such that the primary tissue cut C and the secondary tissue cut C' do not meet or intersect, but a tissue bridge 213 remains between them. As explained before, such arrangement is favorable in view of subsequent adjustments. The distance between the ground of the primary tissue cut C and the secondary tissue cut C', i. e. the width of the tissue bridge 213, may be a cut geometry parameter.

The cut geometry as shown in FIG. 4j is similar to the cut geometry as shown in FIG. 4g. For the cut geometry of FIG. 4j, however, an inclined primary tissue cut C and a further inclined primary tissue cut $C_2$ are implemented, that meet with the edges of the secondary tissue cut C'. Such arrangement is also favorable in order to avoid gaping wounds respectively to improve wound closure.

The cut geometry as shown in FIG. 4k is similar to the cut geometry as shown in FIG. 4j. The primary tissue cut C and the further primary tissue cut $C_2$, however, are inclined into the opposite direction as compared to the cut geometry of FIG. 4j, that is radially outwards from the secondary tissue cut C', rather than inwards as in FIG. 4j. This geometry reduces stress gradients, but requires more space.

The cut geometry as shown in FIG. 4l is similar to the cut geometry as shown in FIG. 4a. The secondary tissue cut C', however has a peripheral region $C_P$' along its edges that extends towards the anterior (outer) cornea surface 211. As explained before, such cut geometry favorably avoids stress peaks along the periphery of the secondary tissue cut C'. A similar further cut geometry is shown in FIG. 4m. While the peripheral regions $C_P$' extend straight in FIG. 4l, they extend towards the anterior (outer) cornea surface in an arc in FIG. 4m. The design and dimensions of the peripheral region $C_P$' may be defined by one or more cut geometry parameters.

Figure 5:
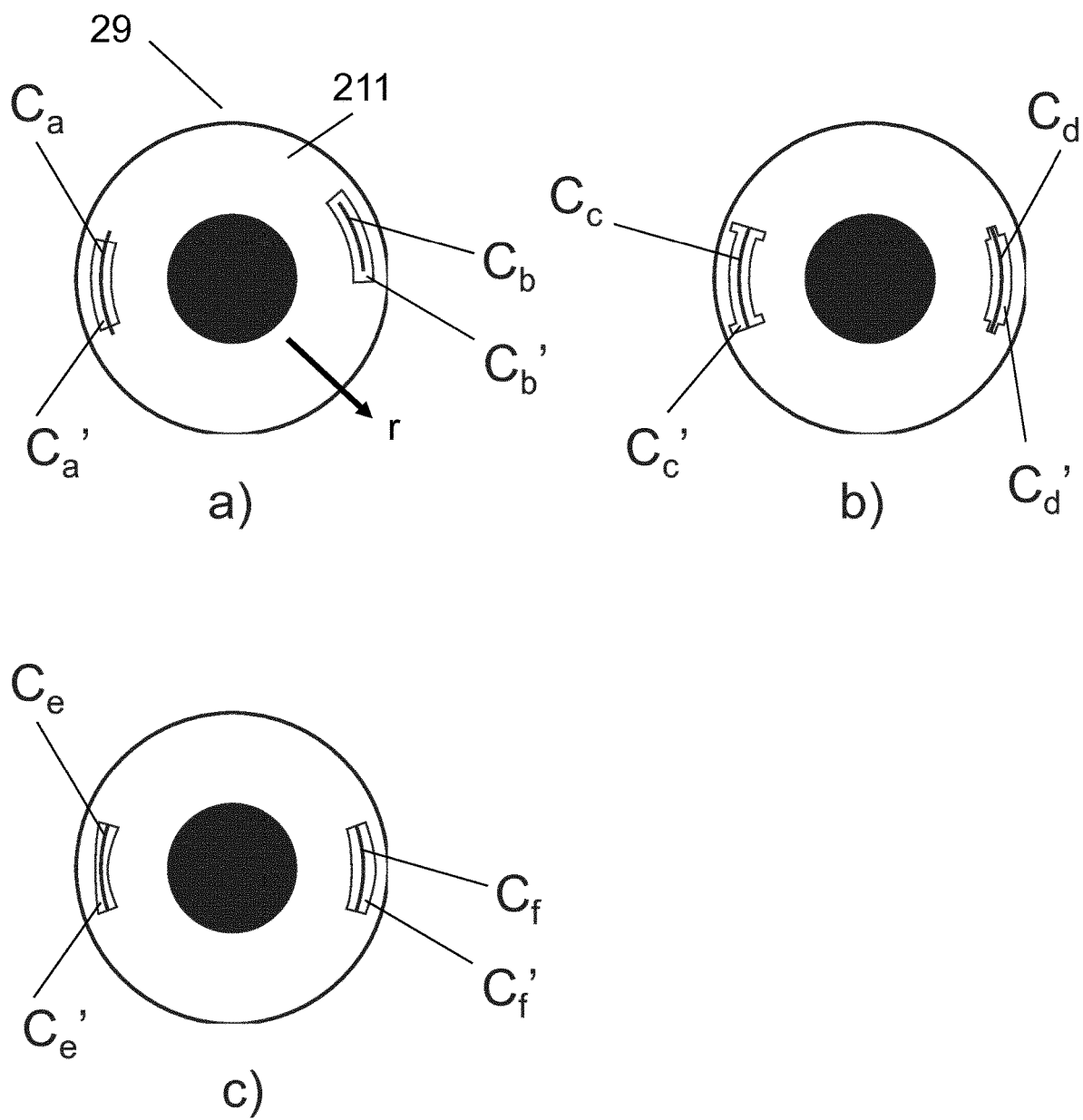
FIG. 5a-5c illustrate exemplary embodiments of cut geometries in a frontal view.

In the following, reference is additionally made to FIG. 5a-FIG. 5c, showing different cut geometries in a frontal view with the viewing direction being along the optical axis onto the cornea surface 211, with the cornea being circumferentially surrounded by the limbus and the sclera 29 (see also FIG. 3). For the sake of conciseness, each of FIG. 5a to FIG. 5c shows two cut geometries. This does not imply, however, that they would be implemented in these specific combinations.

FIG. 5a shows two cut geometries where the primary tissue cut $C_a$ respectively $C_b$ and the corresponding secondary tissue cut $C_a$' respectively $C_b$' are perpendicular with respect to each other, and where the secondary tissue cut $C_a$' respectively $C_b$' is radially symmetrical with respect to the primary tissue cut tissue cut $C_a$ respectively $C_b$, in accordance with FIG. 4a. For $C_a$, $C_a$', the primary tissue cut $C_a$ projects beyond the secondary tissue cut $C_a$' and covers a larger circumferential angle as compared to the secondary tissue cut $C_a$'. For the cut geometry $C_b$, $C_b$' in contrast, the secondary tissue cut $C_b$' projects beyond the primary tissue cut $C_b$, and accordingly covers a larger circumferential angle as compared to the primary tissue cut $C_b$. FIG. 5a also shows that opposite geometries do not necessary have to be placed symmetrically to each other and being of same size respectively dimensions.

FIG. 5b shows two further examples cut geometries with the width of the secondary tissue cut $C_c$' respectively $C_d$' varying along its arc length. In contrast to the embodiments of FIG. 5c, however, the width of the secondary tissue cut $C_c$' respectively $C_d$' does not vary continuously, but in discrete steps respectively at discrete positions along the arc length. Secondary tissue cuts of varying width may be used to achieve a homogenous deformation across the eye.

FIG. 5c shows two examples of cut geometries with the width s of the secondary tissue cut $C_e'$ respectively $C_f'$ continuously varies along its arc length. Exemplarily, the primary tissue cuts $C_e$ respectively $C_f$ are shown as being flush with the corresponding second tissue cuts $C_e$ respectively $C_f$, i. e. cover the same circumferential angle but varying the width s differently.

FIG. 5a-5c exemplarily show the secondary tissue cuts as single continuous cuts. Alternatively, however, they may be implemented by a number of secondary sub-cuts along it circumferential length, with the secondary sub-cuts being separated by tissue bridges.

The invention claimed is:

1. An ophthalmological treatment apparatus for modifying a shape of a corneal surface of a human eye of a patient, including:
 a surgical laser device for implementing tissue cuts; and
 a computerized control device in operative coupling with the surgical laser device, the control device being designed to control the laser device to implement tissue cuts according to a patient-specific cut geometry with a primary tissue cut and a secondary tissue cut,
 wherein the primary tissue cut is a relief cut and extends into the depth of the tissue and includes a patient-specific arc length,
 wherein the secondary tissue cut lies within the tissue, such that the secondary tissue cut adds to the relieving effect of the primary tissue cut,
 wherein the secondary tissue cut is arranged such that it extends in the tissue an area of increased mechanical stress resulting from the primary tissue cut, thereby increasing a corneal tissue deformation resulting from the primary tissue cut, and
 wherein the primary tissue cut and the secondary tissue cut intersect along a joint line.

2. The ophthalmological treatment apparatus according to claim 1, wherein the surgical laser device includes a femtosecond laser source.

3. The ophthalmological treatment apparatus according to claim 1, wherein the primary tissue cut extends to an outer tissue surface.

4. The ophthalmological treatment apparatus according to claim 1, wherein the primary tissue cut and the secondary tissue cut are spatially curved.

5. The ophthalmologic treatment apparatus according to claim 1, wherein the primary tissue cut and the secondary tissue cut are perpendicular with respect to each other.

6. The ophthalmologic treatment apparatus according to claim 1, wherein the secondary tissue cut extends in a constant distance from a posterior corneal surface.

7. The ophthalmologic treatment apparatus according to claim 1, wherein the control device is designed to control the surgical laser device to implement the secondary tissue cut prior to implementing the primary tissue cut.

8. The ophthalmologic treatment apparatus according to claim 1 wherein the control device is designed to control the surgical laser device to start implementing the primary tissue cut at a starting position within the tissue and advance towards the outer tissue surface.

9. The ophthalmological treatment apparatus according to claim 1, wherein the secondary tissue cut is inclined to the primary tissue cut.

10. The ophthalmologic treatment apparatus according to claim 1 wherein the primary tissue cut and the secondary tissue cut are centered with respect to a same axis.

11. An ophthalmological treatment apparatus for modifying a shape of a corneal surface of a human eye of a patient, including:
 a surgical laser device for implementing tissue cuts; and
 a computerized control device in operative coupling with the surgical laser device, the control device being designed to receive patient-specific cut information of a primary tissue cut, wherein the primary tissue cut is a relief cut and extends into the depth of the tissue and includes a patient-specific arc length, and to control the surgical laser device to implement a patient-specific secondary tissue cut,
 wherein the secondary tissue cut lies within the tissue, such that the secondary tissue cut adds to the relieving effect of the primary tissue cut,
 wherein the secondary tissue cut is arranged such that it extends in the tissue an area of increased mechanical stress resulting from the primary tissue cut, thereby increasing a corneal tissue deformation resulting from the primary tissue cut, and
 wherein the primary tissue cut and the secondary tissue cut intersect along a joint line.

12. The ophthalmological treatment apparatus according to claim 11, wherein the secondary tissue cut is perpendicular to the primary tissue cut.

13. The ophthalmological treatment apparatus according to claim 11, wherein the secondary tissue cut is inclined to the primary tissue cut.

14. A method for modifying a shape of a corneal surface of a human eye of a patient comprising:
 implementing, by a surgical laser device, tissue cuts;
 controlling, by a computerized control device in operative coupling with the surgical laser device, the surgical laser device to implement the tissue cuts according to a patient-specific cut geometry with a primary tissue cut and a secondary tissue cut,
 wherein the primary tissue cut is a relief cut and extends into the depth of the tissue and includes a patient-specific arc length,
 wherein the secondary tissue cut lies within the tissue, such that the secondary tissue cut adds to the relieving effect of the primary tissue cut,
 wherein the secondary tissue cut is arranged such that it extends in the tissue an area of increased mechanical stress resulting from the primary tissue cut, thereby increasing a corneal tissue deformation resulting from the primary tissue cut, and
 wherein the primary tissue cut and the secondary tissue cut intersect along a joint line.

\* \* \* \* \*